US007906489B2

(12) United States Patent
Shue et al.

(10) Patent No.: US 7,906,489 B2
(45) Date of Patent: Mar. 15, 2011

(54) 18-MEMBERED MACROCYCLES AND ANALOGS THEREOF

(75) Inventors: Youe-Kong Shue, Carlsbad, CA (US); Chan-Kou Hwang, San Diego, CA (US); Yu-Hung Chiu, San Diego, CA (US); Alex Romero, San Diego, CA (US); Farah Babakhani, San Diego, CA (US); Pamela Sears, San Diego, CA (US); Franklin Okumu, Oakland, CA (US)

(73) Assignee: Optimer Pharmaceuticals, Inc., San Diego, CA (US)

( * ) Notice: Subject to any disclaimer, the term of this patent is extended or adjusted under 35 U.S.C. 154(b) by 762 days.

(21) Appl. No.: 11/882,219

(22) Filed: Jul. 31, 2007

(65) Prior Publication Data
US 2008/0269145 A1    Oct. 30, 2008

Related U.S. Application Data

(63) Continuation-in-part of application No. PCT/US2005/002887, filed on Jan. 31, 2005.

(60) Provisional application No. 60/570,697, filed on May 14, 2004.

(51) Int. Cl.
*A01N 43/04* (2006.01)
*A61K 31/70* (2006.01)

(52) U.S. Cl. ........................... 514/28; 514/867

(58) Field of Classification Search .............. 514/28, 514/867
See application file for complete search history.

(56) References Cited

U.S. PATENT DOCUMENTS

| | | | |
|---|---|---|---|
| 3,978,211 | A | 8/1976 | Coronelli et al. |
| 4,918,174 | A | 4/1990 | Mc Alpine et al. |
| 5,583,115 | A | 12/1996 | McAlpine et al. |
| 5,767,096 | A | 6/1998 | Hochlowski et al. |
| 7,378,508 | B2 | 5/2008 | Chiu et al. |
| 2006/0257981 | A1 | 11/2006 | Shue et al. |
| 2007/0105791 | A1 | 5/2007 | Sears et al. |
| 2007/0173462 | A1 | 7/2007 | Shue et al. |
| 2007/0259949 | A1 | 11/2007 | Chiu et al. |
| 2008/0194497 | A1 | 8/2008 | Chiu et al. |
| 2009/0163428 | A1 | 6/2009 | Chiu et al. |
| 2010/0009925 | A1 | 1/2010 | Shue et al. |
| 2010/0010076 | A1 | 1/2010 | Chiu et al. |
| 2010/0035833 | A1 | 2/2010 | Ichikawa et al. |
| 2010/0081800 | A1 | 4/2010 | Chiu et al. |

FOREIGN PATENT DOCUMENTS

| | | |
|---|---|---|
| WO | WO 96/35702 | 11/1996 |
| WO | WO 2004/014295 | 2/2004 |
| WO | WO 2005/112990 | 12/2005 |
| WO | WO 2006/085838 | 8/2006 |

OTHER PUBLICATIONS

Vippagunta, S.R., Brittain, H.G., Grant, D.J.W. (2001) Crystalline solids. Advanced Drug Delivery Reviews, vol. 48, pp. 3-26.*
Morissette, S.L., Almarsson, Ö., Peterson, M.L., Remenar, J.F., Read, M.J., Lemmo, A.V., Ellis, S., Cima, M.J., Gardner, C.R. (2004) High-throughput crystallization: polymorphs, salts, co-crystals and solvates of pharmaceutical solids. Advanced Drug Delivery Reviews, vol. 56, pp. 275-300.*
Finegold, S.M., Molitoris, D., Vaisanen, M-L., Song, Y., Liu, c., Bolaños, M. (2004) In Vitro Activities of OPT-80 and Comparator Drugs against Intestinal Bacteria. Antimicrobial Agents and Chemotherapy, vol. 48, No. 12, p. 4898-4902.*
Gerding, D.N., Johnson, S., Peterson, L.R., Mulligan, M.E., Silva, Jr., J. (1995) Clostridium Difficile-Associated Diarrhea and Colitis. Infection Control and Hosptial Epidemiology, vol. 16, No. 8, p. 459-477.*
Ansel, H.C., Allen, Jr., L.V., Popovich, N.G. (1999) Pharmaceutical Dosage Forms and Drug Delivery Systems. Published by Lippincott Williams & Wilkins, p. 23-26, 179-180 and 196.*
Credito et al, Antimicrobial Agents and Chemotherapy, Nov. 2004, p. 4430-4434 vol. 48, No. 11.
K.L. Credito, P.C. Appelbaum, "Antianaerobic Activity of OPT 80 Compared to Other Agents," Hershey Medical Center Department of Pathology, (poster), 44th ICAAC (Oct. 30-Nov. 2, 2004) in Chicago.
Babakhani et al., "Narrow spectrum activity and low fecal protein binding of Opt-80 and its major hydrolysis metabolite (OP-1118)", Program and Abstract of the 47th Interscience Conference on Antimicrobial Agents and Chemotherapy, Chicago, IL, p. 212 (2007), XP008103008.
Gerber et al., "OPT-80, a macrocyclic antimicrobial agent for the treatment of clostridium difficile infections: a review", Expert Opinion on Investigational Drugs, 17(4), p. 547-53 (2008), XP002479935.
Lewiston et al., "Determination of OPT-80 and its desisobutyryl metabolite (OP-1118) in human plasma by a LC/MS/MS method", AAPS Journal, American Association of Pharmaceutical Scientists, (2005), XP008103043.
Okumu et al., "Safety and pharmacokinetics of OPT-80, a novel antibiotic for treatment of clostridium difficile associated diarrhea (CDAD)", Program and Abstract of the 44th Interscience Conference on Antimicrobial Agents and Chemotherapy, p. 204, (2004), XP008103005.
Shangle et al., "Safety and pharmacokinetics of OPT-80 in human volunteers", Program and Abstract of the 44th Interscience Conference on Antimicrobial Agents and Chemotherapy, Washington, DC, p. 1 (2004), XP008103010.

(Continued)

*Primary Examiner* — Shaojia Anna Jiang
*Assistant Examiner* — Scarlett Goon
(74) *Attorney, Agent, or Firm* — Morgan Lewis & Bockius LLP

(57) ABSTRACT

The present invention relates generally to the 18-membered macrocyclic antimicrobial agents called Tiacumicins, specifically, OPT-80 (which is composed almost entirely of the R-Tiacumicin B), pharmaceutical compositions comprising OPT-80, and methods using OPT-80. In particular, this compound is a potent drug for the treatment of bacterial infections, specifically *C. difficile* infections.

14 Claims, 1 Drawing Sheet

OTHER PUBLICATIONS

Shue et al., "Safety, tolerance, and pharmacokinetics studies of OPT-80 in healthy volunteers following single and multiple oral doses", Antimicrobial Agents and Chemotherapy, 52(4), p. 1391-1395 (2008), XP002517908.

Cambridge Crystallographic Data Centre Deposition No. 100349, (2000), CCDC No. 114782.

Chemical Abstracts registry entry 56645-60-4, Tiacumicin B, Copyright 2007, American Chemical Society, pp. 1-2.

Braga et al., "Making crystals from crystals: a green route to crystal engineering and polymorphism" Chemical Communications (2005) pp. 3635-3645.

Pharmaceutical Dosage Forms: Tablets, vol. 2, Published by Marcel Dekker, Inc., ed. by Lieberman, Lachman, and Schwartz, pp. 462-472, (1990).

Dean, J., Analytical Chemistry Handbook, Published by McGraw-Hill, Inc., pp. 10.23-10.26, (1995).

Jain et al., "Polymorphism in Pharmacy" Indian Drugs (1986) vol. 23, No. 6, pp. 315-329.

Swanson, R.N. et al., In Vitro and In Vivo Evaluation of Tiacumicins B and C against *Clostridium difficile, Antimicrob. Agents Chemother.*, Jun. 1991, pp. 1108-1111.

Hochlowski, J.E. et al., Tiacumicins, A Novel Complex of 18-Membered Macrolides, *J. Antibiotics*, vol. XL, No. 5, pp. 575-588 (May 1987).

Arnone et al. "Structure Elucidation of the Macrocyclic Antibiotic Lipiarmycin" Journal of the Chemical Society, Perkin Transactions 1, Chemical Society, 1353-1359 (1987).

Caira "Crystalline Polymorphism of Organic Compounds" Topics in Current Chemistry 198:163-208 (1998).

Poduval et al. "Clostridium difficile and vancomycin-resistant enterococcus: the new nosocomial alliance" The American Journal of Gastroenterology 95(12):3513-3515 (2000).

Polymorphism in Pharmaceutical Solids, published 1999 by Marcel Dekker Inc, ed. By Harry G. Brittain, pp. 1-2.

The Condensed Chemical Dictionary, Tenth Edition, published 1981 by the Van Nostrand Reinhold Company, revised by Gessner G. Hawley, p. 35 and 835.

Theriault et al. "Tiacumicins, a novel complex of 18-membered macrolide antibiotics. I. Taxonomy, fermentation . . . " J Antibiot (Tokyo) 40(5):567-574 (1987).

Supplementary European Search Report issued in the corresponding European Patent Application No. 05712354.9 (Jan. 15, 2010).

\* cited by examiner

18-MEMBERED MACROCYCLES AND ANALOGS THEREOF

CROSS-REFERENCE TO RELATED APPLICATIONS

The present application is a continuation-in-part application of International Application PCT/US2005/002887 filed Jan. 31, 2005, and claims priority to U.S. Provisional Application No. 60/570,697 filed May 14, 2004, each application of which is incorporated by reference in its entirety.

FIELD OF INVENTION

The present invention relates generally to the 18-membered macrocyclic antimicrobial agents called Tiacumicins, specifically, the R-Tiacumicin B or Tiacumicin B and its related compounds. In particular, substantially pure R-Tiacumicin B, as a potent antibiotic agent for the treatment of bacterial infections, specifically GI infections caused by toxin producing strains of *Clostridium difficile* (*C. difficile*), *Staphylococcus aureus* (*S. aureus*) including methicillin-resistant *Staphylococcus aureus* (MRSA) and *Clostridium perfringens* (*C. perfringens*).

BACKGROUND OF THE INVENTION

Macrocycles are an important therapeutic class of antibiotics. These compounds are frequently produced as a family of closely related biogenetic congeners. The Tiacumicins are a series of 18-membered macrocyclic antibiotics in which the macrocyclic ring is glycosidically attached to one or two sugars. A seven-carbon sugar is esterfied at various positions with small fatty acids. The other sugar, when present, is esterfied with an isomer of the fully substituted benzoic acid, everninic acid. (Journal of Liquid Chromatography, 1988, 11: 191-201).

Tiacumicins are a family of related compounds that contain the 18-membered ring shown in Formula I below.

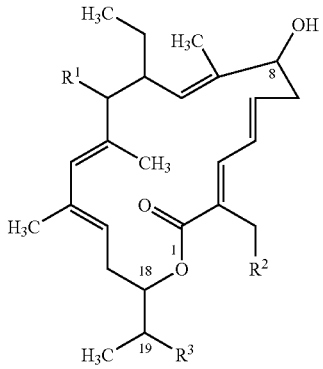

Formula I

At present, several distinct Tiacumicins have been identified and six of these (Tiacumicin A-F) are defined by their particular pattern of substituents $R^1$, $R^2$, and $R^3$ (U.S. Pat. No. 4,918,174; J. Antibiotics, 1987, 40: 575-588), as shown in Table 1.

TABLE 1

Substituents Present In Tiacumcins A-F

| | $R^1$ | $R^2$ | $R^3$ |
|---|---|---|---|
| A | sugar | H | H |
| B | sugar | sugar-benzoate | OH |
| C | sugar | sugar-benzoate | OH |

TABLE 1-continued

Substituents Present In Tiacumicins A-F

| | R¹ | R² | R³ |
|---|---|---|---|
| D | (structure) | (structure) | OH |
| E | (structure) | (structure) | OH |
| F | (structure) | (structure) | OH |

Tiacumicins A-F have been characterized spectroscopically and by other physical methods. The chemical structures of Tiacumicins are based on spectroscopy: UV-vis, IR and $^1$H and $^{13}$C NMR, see for example J. Antibiotics, 1987, 40: 575-588. Inspection of Table 1 reveals that certain members of the family are structurally related isomers and/or differ by the presence or absence of certain moieties. Others differ in the nature of their ester groups.

Tiacumicins are produced by bacteria, including *Dactylosporangium aurantiacum* subspecies *hamdenensis*, which may be obtained from the ARS Patent Collection of the Northern Regional Research Center, United States Department of Agriculture, 1815 North University Street, Peoria, Ill. 61604, accession number NRRL 18085. The characteristics of strain AB 718C-41 are given in J. Antibiotics, 1987, 40: 567-574 and U.S. Pat. No. 4,918,174.

*C. difficile*-associated diarrhea (CDAD) is a disease characterized by severe and painful diarrhea. *C. difficile* is responsible for approximately 20% of the cases of antibiotic-associated diarrhea (AAD) and the majority of the cases of antibiotic-associated colitis (AAC). These diseases are typically caused by toxin producing strains of *C. difficile, S. aureus* including methicillin-resistant *S. aureus* (MRSA) and *Clostridium perfringens* (*C. perfringens*). AAD represents a major economic burden to the healthcare system that is conservatively estimated at $3-6 billion per year in excess hospital costs in the U.S. alone.

Vancomycin-resistant enterococci, for which intestinal colonization provides a constant reservoir for infection, has also emerged as a major nosocomial pathogen associated with increased health care cost and mortality. VRE can appear as coinfection in patients infected with *C. difficile*, or more commonly cause infection in certain high risk patients such as haematology and oncology patients, patients in intensive care units and patients receiving solid organ transplants.

Methicillin-resistant Staphylococci, such as MRSA, are increasing in prevalence in both the hospital and community settings. Staphylococci are found on the skin and within the digestive and respiratory tracts but can infect open wounds and burns and can progress to serious systemic infection. The emergence of multi-drug resistant Staphylococci, especially, in the hospital where antibiotic use is frequent and selective pressure for drug-resistant organisms is high, has proven a challenge for treating these patients. The presence of MRSA on the skin of patients and health care workers promotes transmission of the multi-drug resistant organisms.

Similar diseases, including but not limited to clostridial enterocolitis, neonatal diarrhea, antibiotic-associated enterocolitis, sporadic enterocolitis, and nosocomial enterocolitis are also significant problems in some animal species.

AAD is a significant problem in hospitals and long-term care facilities and in the community. *C. difficile* is the leading cause of AAD in the hospital setting, accounting for approximately 20% of cases of AAD and the majority of cases of antibiotic-associated colitis (AAC). The rising incidence of *Clostridium difficile*-associated diarrhea (CDAD) has been attributed to the frequent prescription of broad-spectrum antibiotics to hospitalized patients.

The most serious form of the disease is pseudomembranous colitis (PMC), which is manifested histologically by colitis with mucosal plaques, and clinically by severe diarrhea, abdominal cramps, and systemic toxicity. The overall mortality rate from CDAD is low, but is much greater in patients who develop severe colitis or systemic toxicity. A recent study has shown that even when death is not directly attributable to *C. difficile*, the rate of mortality in CDAD patients as compared to case-matched controls is much greater.

Diarrhea and colitis are caused by the elaboration of one or more *C. difficile* toxins. The organism proliferates in the colon in patients who have been given broad-spectrum antibiotics or, less commonly, cancer chemotherapy. CDAD is diagnosed in approximately 20% of hospitalized patients who develop diarrhea after treatment with such agents.

There are currently two dominant therapies for CDAD: vancomycin and metronidazole. Vancomycin is not recommended for first-line treatment of CDAD mainly because it is the only antibiotic active against some serious life-threatening multi-drug resistant bacteria. Therefore, in an effort to minimize the emergence of vancomycin-resistant *Enterococcus* (VRE) or vancomycin-resistant *S. aureus* (VRSA), the medical community discourages the use of this drug except when absolutely necessary.

Metronidazole is recommended as initial therapy out of concern for the promotion and selection of vancomycin resistant gut flora, especially enterococci. Despite reports that the frequency of *C. difficile* resistance may be >6% in some countries, metronidazole remains nearly as effective as vancomycin, is considerably less expensive, and can be used either orally or intravenously. Metronidazole is associated with significant adverse effects including nausea, neuropathy, leukopenia, seizures, and a toxic reaction to alcohol. Furthermore, it is not safe for use in children or pregnant women. Clinical recurrence occurs in up to 20% of cases after treatment with either vancomycin or metronidazole. Therapy with metronidazole has been reported to be an important risk factor for VRE colonization and infection. The current treatment regime against Gastrointestinal infections, e.g., *Clostridium difficile*-associated diarrhea (CDAD) is rather cumbersome, requiring up to 500 mg four-times daily for 10 to 14 days. Thus, there is a need for better treatment for cases of CDAD as well as for cases of other Antibiotic-associated diarrhea (AAD) and Antibiotic-associated colitis (AAC).

Tiacumicins, specifically Tiacumicin B, show activity against a variety of bacterial pathogens and in particular against *C. difficile*, a Gram-positive bacterium (Antimicrob. Agents Chemother. 1991, 1108-1111). *C. difficile* is an anaerobic spore-forming bacterium that causes an infection of the bowel. Diarrhea is the most common symptom but abdominal pain and fever may also occur. *C. difficile* is a major causative agent of colitis (inflammation of the colon) and diarrhea that may occur following antibiotic intake. This bacterium is primarily acquired in hospitals and chronic care facilities. Because Tiacumicin B shows promising activity against *C. difficile*, it is expected to be useful in the treatment of bacterial infections, especially those of the gastrointestinal tract, in mammals. Examples of such treatments include but are not limited to treatment of colitis and treatment of irritable bowel syndrome. Tiacumicins may also find use for the treatment of gastrointestinal cancers.

Tiacumicin antibiotics are described in U.S. Pat. No. 4,918, 174 (issued Apr. 17, 1990), J. Antibiotics 1987, 40: 575-588, J. Antibiotics 1987, 40: 567-574, J. Liquid Chromatography 1988, 11: 191-201, Antimicrobial Agents and Chemotherapy 1991, 35: 1108-1111, U.S. Pat. No. 5,583,115 (issued Dec. 10, 1996), and U.S. Pat. No. 5,767,096 (issued Jun. 16, 1998), which are all incorporated herein by reference. Related compounds are the Lipiarmycin antibiotics (c.f., J. Chem. Soc. Perkin Trans. I, 1987, 1353-1359 and J. Antibiotics 1988, 41: 308-315) and the Clostomicin antibiotics (J. Antibiotics 1986, 39: 1407-1412), which are all incorporated herein by reference.

SUMMARY OF THE INVENTION

The present invention relates to new pharmaceutical compositions containing R-Tiacumicins, specifically the optically pure R-Tiacumicin B, and to the use of these new compositions in combination with existing drugs to treat infections caused by gram-positive anerobes.

One embodiment of the present invention is directed towards the discovery that the chiral center at C-19 of Tiacumicin B has great effect on biological activity. It has now been discovered that a substantially pure preparation of higher activity R-Tiacumicin B, which has an R-hydroxy group at C-19 has surprisingly lower MIC values than the optically pure S-isomer of Tiacumicin B and other Tiacumicin B related compounds.

In another embodiment of the present invention the substantially pure R-Tiacumicin B has an unusually long postantibiotic activity (PAE).

This invention encompasses the composition of novel antibiotic agents, containing substantially pure R-Tiacumicins, by submerged aerobic fermentation of the microorganism *Dactylosporangium aurantiacum* subspecies *hamdenensis*. The production method is covered by WO 2004/014295 A2, which is hereby incorporated by reference.

DETAILED DESCRIPTION OF THE INVENTION

Definitions

Figure 1:
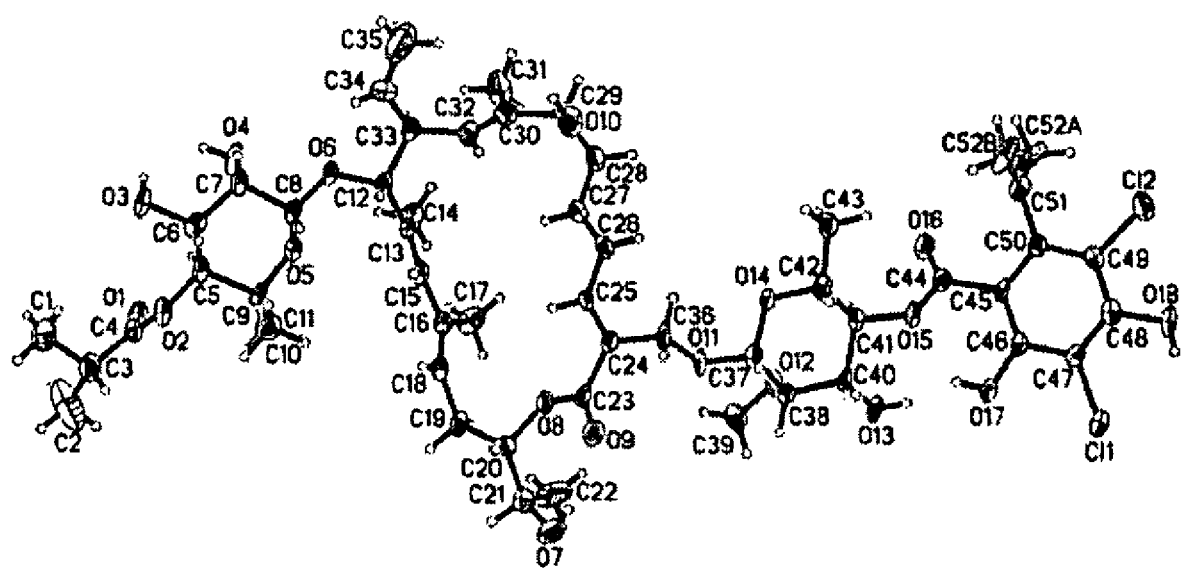
FIG. 1 shows the Oak Ridge Thermal Ellipsoid Plot Program (ORTEP) chemical structure of R-Tiacumicin B.

The term "antibiotic-associated condition" refers to a condition resulting when antibiotic therapy disturbs the balance of the microbial flora of the gut, allowing pathogenic organisms such as enterotoxin producing strains of *C. difficile, S. aureus* and *C. perfringens* to flourish. These organisms can cause diarrhea, pseudomembranous colitis, and colitis and are manifested by diarrhea, urgency, abdominal cramps, tenesmus, and fever among other symptoms. Diarrhea, when severe, causes dehydration and the medical complications associated with dehydration.

The term "asymmetrically substituted" refers to a molecular structure in which an atom having four tetrahedral valences is attached to four different atoms or groups. The commonest cases involve the carbon atom. In such cases, two optical isomers (D- and L-enantiomers or R- and S-enantiomers) per carbon atom result which are nonsuperposable mirror images of each other. Many compounds have more than one asymmetric carbon. This results in the possibility of many optical isomers, the number being determined by the formula 2", where n is the number of asymmetric carbons.

As used herein, and unless otherwise indicated, the terms "biohydrolyzable carbamate," "biohydrolyzable carbonate," "biohydrolyzable ureide" and "biohydrolyzable phosphate" mean a carbamate, carbonate, ureide and phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein, and unless otherwise indicated, the term "biohydrolyzable ester" means an ester of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, alkoxyacyloxy esters, alkyl acylamino alkyl esters, and choline esters.

As used herein, and unless otherwise indicated, the term "biohydrolyzable amide" means an amide of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable amides include, but are not limited to, lower alkyl amides, .alpha.-amino acid amides, alkoxyacyl amides, and alkylaminoalkylcarbonyl amides.

The term "broth" as used herein refers to the fluid culture medium as obtained during or after fermentation. Broth comprises a mixture of water, the desired antibiotic(s), unused nutrients, living or dead organisms, metabolic products, and the adsorbent with or without adsorbed product.

The term "C-19 Ketone" refers to a Tiacumicin B related compound shown below in Formula II:

The term "diastereomers" refers to stereoisomers that are not mirror images of each other.

The term "enantiomer" refers to a non-superimposable mirror image of itself. An enantiomer of an optically active isomer rotates plane polarized light in an equal but opposite direction of the original isomer. A solution of equal parts of an optically active isomer and its enantiomer is known as a racemic solution and has a net rotation of plane polarized light of zero. Enantiomers will have the opposite prefixes of each other: D- becomes L- or R- becomes S-. Often only one enantiomer is active in a biological system, because most biological reactions are enzymatic and the enzymes can only attach to one of the enantiomers.

The term "excipient" refers to an inert substance added to a pharmacological composition to further facilitate administration of a compound. Examples of excipients include but are not limited to, calcium carbonate, calcium phosphate, various sugars and types of starch, cellulose derivatives, gelatin, vegetable oils and polyethylene glycols.

The term "halogen" includes F, Cl, Br and I.

As used herein, the term "hydrate" means a compound of the present invention or a salt thereof that further includes a stoichiometric or non-stoichiometric amount of water bound by non-covalent intermolecular forces.

The term "isomeric mixture" means a mixture of two or more configurationally distinct chemical species having the same chemical formula. An isomeric mixture is a genus comprising individual isomeric species. Examples of isomeric mixtures include stereoisomers (enantiomers and diastereomers), regioisomers, as might result for example from a pericyclic reaction. The compounds of the present invention comprise asymmetrically substituted carbon atoms. Such asymmetrically substituted carbon atoms can result in mixtures of stereoisomers at a particular asymmetrically substituted carbon atom or a single stereoisomer. As a result, racemic mixtures, mixtures of diastereomers, as well as single diastereomers of the compounds of the invention are included in the present invention.

Formula II

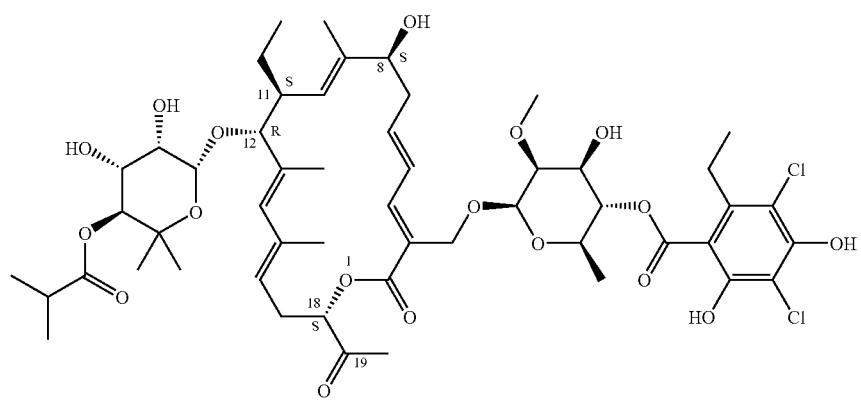

The term "Lipiarmycin A4" refers to a Tiacumicin B related compound shown below in Formula III:

Formula III

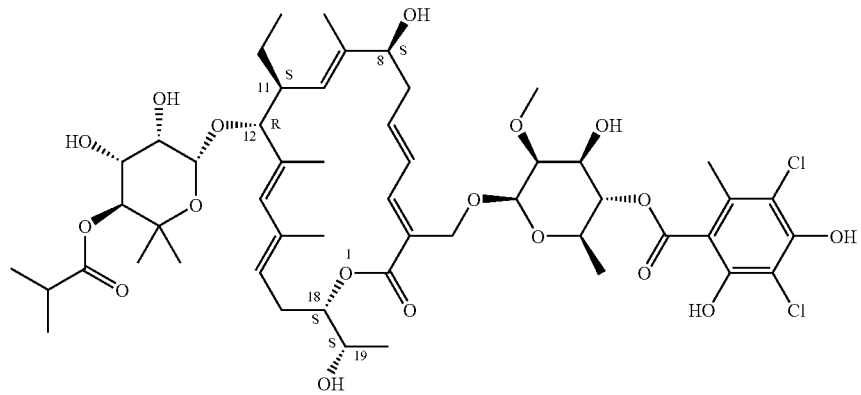

The term "lower alkyl," alone or in combination, refers to an optionally substituted straight-chain or optionally substituted branched-chain having from 1 to about 8 carbons (e.g., $C_1, C_2, C_3, C_4, C_5, C_6, C_7, C_8$), more preferably 1 to 4 carbons (e.g., $C_1$, $C_2$, $C_3$, $C_4$). Examples of alkyl radicals include methyl, ethyl, n-propyl, isopropyl, n-butyl, isobutyl, sec-butyl, tert-butyl. A "lower alkyl" is generally a shorter alkyl, e.g., one containing from 1 to about 4 carbon atoms (e.g., $C_1$, $C_2$, $C_3$, $C_4$).

The term "macrocycles" refers to organic molecules with large ring structures usually containing over 10 atoms.

The term "18-membered macrocycles" refers to organic molecules with ring structures containing 18 atoms.

The term "membered ring" can embrace any cyclic structure, including carbocycles and heterocycles as described above. The term "membered" is meant to denote the number of skeletal atoms that constitute the ring. Thus, for example, pyridine, pyran and thiopyran are 6 membered rings and pyrrole, furan, and thiophene are 5 membered rings.

The term "MIC" or "minimum inhibitory concentration" refers to the lowest concentration of an antibiotic that is needed to inhibit growth of a bacterial isolate in vitro. A common method for determining the MIC of an antibiotic is to prepare several tubes containing serial dilutions of the antibiotic, that are then inoculated with the bacterial isolate of interest. The MIC of an antibiotic can be determined from the tube with the lowest concentration that shows no turbidity (no growth).

The term "$MIC_{50}$" refers to the lowest concentration of antibiotic required to inhibit the growth of 50% of the bacterial strains tested within a given bacterial species.

The term "$MIC_{90}$" refers to the lowest concentration of antibiotic required to inhibit the growth of 90% of the bacterial strains tested within a given bacterial species.

The term "OPT-80" refers to a preparation containing R-Tiacumicin B and Tiacumicin B related compounds (including, but not limited to, Tiacumicins, Lipiarmycin A4 and C-19 Ketone). Preparations of this type are described in detail in PCT application PCT/US03/21977, having an international publication number of WO 2004/014295 A2 and which preparations are incorporated here by reference.

The term "ORTEP" refers to the Oak Ridge Thermal Ellipsoid Plot computer program, written in Fortran, for drawing crystal structure illustrations. Ball-and-stick type illustrations of a quality suitable for publication are produced with either spheres or thermal-motion probability ellipsoids, derived from anisotropic temperature factor parameters, on the atomic sites. The program also produces stereoscopic pairs of illustrations which aid in the visualization of complex arrangements of atoms and their correlated thermal motion patterns.

The term "PAE" or "post-antibiotic effect" refers to a well-established pharmacodynamic parameter that reflects the persistent suppression of bacterial growth following antibiotic exposure.

The term "patient" refers to a human or animal in need of medical treatment. For the purposes of this invention, human patients are typically institutionalized in a primary medical care facility such as a hospital or nursing home. However, treatment of a disease associated with the use of antibiotics or cancer chemotherapies or antiviral therapies can occur on an outpatient basis, upon discharge from a primary care facility, or can be prescribed by a physician for home-care, not in association with a primary medical care facility. Animals in need of medical treatment are typically in the care of a veterinarian.

The term "pharmaceutically acceptable carrier" refers to a carrier or diluent that is pharmaceutically acceptable.

The term "pharmaceutically acceptable salts" refers to those derived from pharmaceutically acceptable inorganic and organic bases. Salts derived from appropriate bases include alkali metal (e.g., sodium or potassium), alkaline earth metal (e.g., magnesium), ammonium and $N(C_1-C_4 \text{ alkyl})_4^+$ salts, and the like. Illustrative examples of some of these include sodium hydroxide, potassium hydroxide, choline hydroxide, sodium carbonate, and the like. The term "pharmaceutically acceptable salt" also refers to salts prepared from pharmaceutically acceptable non-toxic acids, including inorganic acids and organic acids. Suitable non-toxic acids include inorganic and organic acids such as, but not limited to, acetic, alginic, anthranilic, benzenesulfonic, benzoic, camphorsulfonic, citric, ethenesulfonic, formic, fumaric, furoic, gluconic, glutamic, glucorenic, galacturonic, glycidic, hydrobromic, hydrochloric, isethionic, lactic, maleic, malic, mandelic, methanesulfonic, mucic, nitric, pamoic, pantothenic, phenylacetic, propionic, phosphoric, salicylic, stearic, succinic, sulfanilic, sulfuric, tartaric acid, p-toluenesulfonic and the like. Particularly preferred are hydrochloric, hydrobromic, phosphoric, and sulfuric acids, and most particularly preferred is the hydrochloride salt.

The term "pharmaceutical composition" refers to a composition of the R-Tiacumicin described herein, or physiologically acceptable salts thereof, with other chemical components, such as physiologically acceptable carriers and/or excipients. The purpose of a pharmaceutical composition is to facilitate administration of a compound to a mammal, including humans.

The term "physiologically acceptable carrier" refers to a carrier or diluent that does not cause significant irritation to an organism and does not abrogate the biological activity and properties of the administered compound.

As used herein, and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, compounds that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include compounds that comprise —NO, —NO$_2$, —ONO, or —ONO$_2$ moieties. When used to describe a compound of the invention, the term "prodrug" may also to be interpreted to exclude other compounds of the invention for example racemates.

The term "pseudomembranous colitis" or "enteritis" refers to the formation of pseudomembranous material (i.e., material composed of fibrin, mucous, necrotic epithelial cells and leukocytes) due to inflammation of the mucous membrane of both the small and large intestine.

The terms "R" and "S" configuration, as used herein, are as defined by the IUPAC 1974 Recommendations for Section E, Fundamental Stereochemistry, *Pure Appl. Chem.* (1976) 45, 13-30. Chiral molecules can be named based on the atomic numbers of the atoms or groups of atoms, the ligands that are attached to the chiral center. The ligands are given a priority (the higher the atomic number the higher the priority) and if the priorities increase in a clockwise direction, they are said to be R-. Otherwise, if they are prioritized in a counterclockwise direction they are said to be S-.

The term "R-Tiacumicin B" refers to the optically pure (R)-isomer of Tiacumicin B with an (R)-hydroxy group at C-19, as shown below in Formula IV:

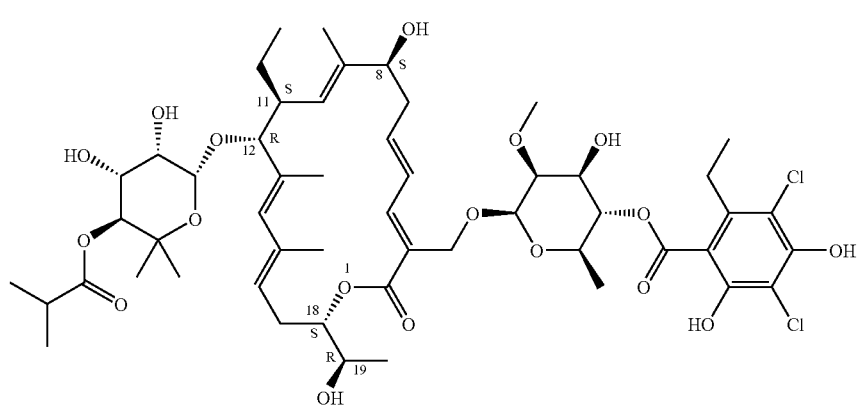

Formula IV

The term "S-Tiacumicin B" refers to the optically pure (S)-isomer of Tiacumicin B with an (S)-hydroxy group at C-19, as shown below in Formula V:

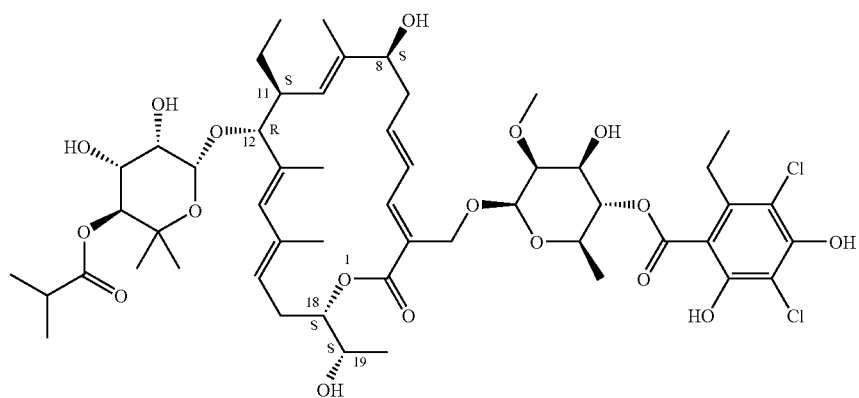

Formula V

The term "stereoisomers" refers to compounds whose molecules have the same number and kind of atoms and the same atomic arrangement, but differ in their spatial arrangement.

As used herein, and unless otherwise indicated, the terms "optically pure," "stereomerically pure," and "substantially stereomerically pure" are used interchangeably and mean one stereoisomer of a compound or a composition that comprises one stereoisomer of a compound and is substantially free of other stereoisomer(s) of that compound. For example, a stereomerically pure compound or composition of a compound having one chiral center will be substantially free of the opposite enantiomer of the compound. A stereomerically pure compound or composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

The term "sugar" generally refers to mono-, di- or oligosaccharides. A saccharide may be substituted, for example, glucosamine, galactosamine, acetylglucose, acetylgalactose, N-acetylglucosamine, N-acetyl-galactosamine, galactosyl-N-acetylglucosamine, N-acetylneuraminic acid (sialic acid), etc., as well as sulfated and phosphorylated sugars. For the purposes of this definition, the saccharides are in their pyranose or furanose form.

The term "Tiacumicin" as used herein refers to a family of compounds all of which comprise the 18-membered macrocycle shown below in Formula I:

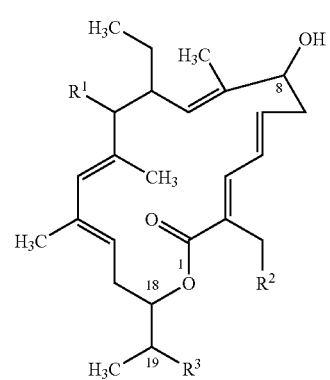

Formula I

The term "Tiacumicin B" as used herein refers to the 18-membered macrocycle shown below in Formula VI:

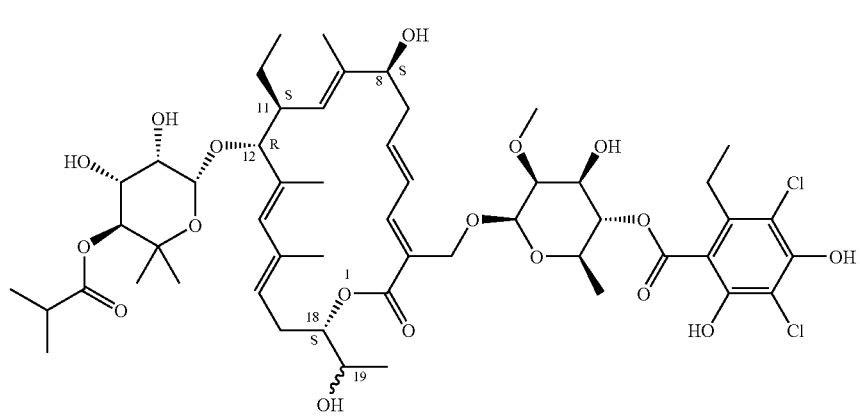

Formula VI

The term "yield" as used herein refers to an amount of crude Tiacumicin re-constituted in methanol to the same volume as the original fermentation broth. Yield is determined using standard HPLC techniques. Yield is reported in units of mg/L.

This invention encompasses the composition of novel antibiotic agents, Tiacumicins, by submerged aerobic fermentation of the microorganism *Dactylosporangium aurantiacum* subspecies *hamdenensis*. The production method is covered by WO 2004/014295 A2.

The present invention relates to new antibacterial compositions containing R-Tiacumicins, specifically the R-Tiacumicin B (which has an R-hydroxyl at C-19), and to the use of these new compositions in combination with existing drugs to treat infections caused by gram-positive anaerobes.

The present invention further relates to stereoisomerically pure Tiacumicin B, which contains 90-100% of the R-stereoisomer, preferably at least 93% of the R-stereoisomer, more preferably 95% of the R-stereoisomer, even more preferably 99% of the R-stereoisomer.

In accordance with the present invention there are provided compounds with the structure of Formula VII:

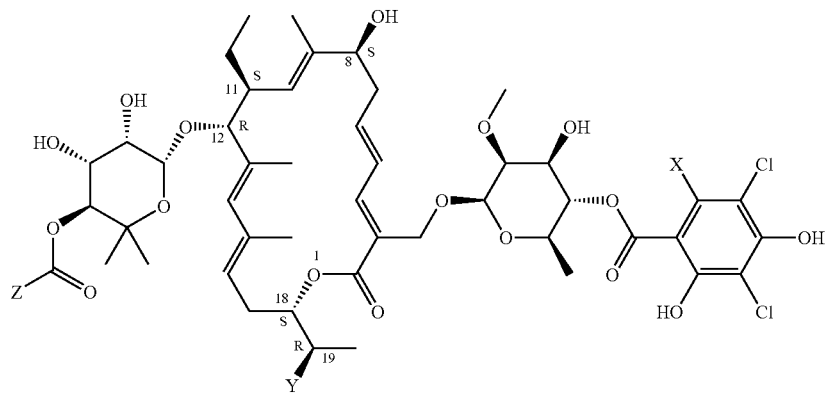

Formula VII wherein:
X is selected from lower alkyl, and wherein the term "lower alkyl" as used herein refers to branched or straight chain alkyl groups comprising one to two carbon atoms, including methyl, ethyl, n-propyl, isopropyl, and the like; and
Y is selected from OH or a ketone (═O); and
Z is selected from H or lower alkyl, and wherein the term "lower alkyl" as used herein refers to branched or straight chain alkyl groups comprising one to five carbon atoms, including methyl, ethyl, propyl, isopropyl, n-butyl, t-butyl, and the like.

Preferred compounds of the invention are compounds of Formula VII wherein X is methyl or ethyl, Y is ketone (═O) or OH and Z is isopropyl.

More preferred compounds of the invention are the compound of the Formula VII wherein X is ethyl, Y is ketone (═O) or OH and Z is isopropyl.

The most preferred compounds of the invention are the compounds of Formula VII wherein X is ethyl, Y is OH R and Z is isopropyl.

One embodiment of the present invention is directed towards the discovery that the chiral center at C-19 of Tiacumicin B has great effect on biological activity. It has now been discovered that R-Tiacumicin B, which has an R-hydroxy group at C-19 has significantly higher activity than the S-Tiacumicin B and other Tiacumicin B related compounds (Lipiarmycin A4 and C-19 Ketone). The higher activity is shown by much lowered MIC values, which can be seen below in Example 3, Tables 3 and 4 for several strains of *C. difficile, S. aureus, E. faecalis,* and *E. faecium.* This effect of the C-19 chiral center on biological activity is an unexpected and novel discovery.

In another embodiment of the present invention OPT-80 (which is composed almost entirely of the R-Tiacumicin B) has an unusually long post-antibiotic effect (PAE). This is discussed below in Example 4, where it is shown that OPT-80 has a PAE of greater than 24 hours. This PAE is unexpectedly longer than the usual antibiotic PAE of 1-5 hours.

The present invention also relates to the disclosure of pharmaceutical compositions, which comprise a compound of the present invention in combination with a pharmaceutically acceptable carrier.

Yet another aspect of the invention discloses a method of inhibiting or treating bacterial infections in humans, comprising administering to the patient a therapeutically effective amount of a compound of the invention alone or in combination with another antibacterial or antifungal agent.

Production

The 18-membered macrocycles and analogs thereof are produced by fermentation. Cultivation of *Dactylosporangium aurantiacum* subsp. *hamdenensis* AB 718C-41 NRRL 18085 for the production of the Tiacumicins is carried out in a medium containing carbon sources, inorganic salts and other organic ingredients with one or more absorbents under proper aeration conditions and mixing in a sterile environment.

The microorganism to produce the active antibacterial agents was identified as belonging to the family *Actinoplanaceae,* genus *Dactylosporangium (J. of Antibiotics,* 1987, 40: 567-574 and U.S. Pat. No. 4,918,174). It has been designated *Dactylasporangium aurantiacum* subspecies *hamdenensis* 718C-41. The subculture was obtained from the ARS Patent Collection of the Northern Regional Research Center, United States Department of Agriculture, 1815 North University Street, Peoria, Ill. 61604, U.S.A., where it was assigned accession number NRRL 18085. The characteristics of strain AB 718C-41 are given in the Journal of Antibiotics, 1987, 40: 567-574 and U.S. Pat. No. 4,918,174.

Methods of isolating stereomerically pure isomers are known in the art. Methods of isolating stereomerically pure R-Tiacumicin include, but are not limited to, recrystallization of the crude mixture in solvents including, aqueous methanol or isopropanol and chiral HPLC.

This invention encompasses the composition of novel antibiotic agents, Tiacumicins, by submerged aerobic fermentation of the microorganism *Dactylosporangium aurantiacum* subspecies *hamdenensis.* The production method is covered by WO 2004/014295 A2, which is hereby incorporated by reference.

Pharmaceutical Formulation and Administration

Pharmaceutical compositions of the Tiacumicin compounds of the present invention, specifically OPT-80 (which is composed almost entirely of the R-Tiacumicin), according to the invention may be formulated to release an antibiotic substantially immediately upon administration or at any predetermined time or time period after administration.

The latter types of compositions are generally known as modified release formulations, which include formulations that create a substantially constant concentration of the drug within the intestinal tract over an extended period of time, and formulations that have modified release characteristics based on temporal or environmental criteria as described in Modified-Release Drug Delivery Technology, ed. M. J. Rathbone, J. Hodgraft and M. S. Roberts. Marcel Dekker, Inc. New York.

Any oral biologically-acceptable dosage form, or combinations thereof, can be employed in the methods of the invention. Examples of such dosage forms include, without limitation, chewable tablets, quick dissolve tablets, effervescent tablets, reconstitutable powders, elixirs, liquids, suppositories, creams, solutions, suspensions, emulsions, tablets, multi-layer tablets, bi-layer tablets, capsules, soft gelatin capsules, hard gelatin capsules, osmotic tablets, osmotic capsules, caplets, lozenges, chewable lozenges, beads, powders, granules, particles, microparticles, dispersible granules, ingestibles, infusions, health bars, confections, animal feeds, cereals, cereal coatings, foods, nutritive foods, functional foods and combinations thereof. The preparation of any of the above dosage forms is well known to persons of ordinary skill in the art. Additionally, the pharmaceutical formulations may be designed to provide either immediate or controlled release of the antibiotic upon reaching the target site. The selection of immediate or controlled release compositions depends upon a variety of factors including the species and antibiotic susceptibility of Gram-positive bacteria being treated and the bacteriostatic/bactericidal characteristics of the therapeutics. Methods well known in the art for making formulations are found, for example, in Remington: The Science and Practice of Pharmacy (20th ed.), ed. A. R. Gennaro, 2000, Lippincott Williams & Wilkins, Philadelphia, or in Encyclopedia of Pharmaceutical Technology, eds. J. Swarbrick and J. C. Boylan, 1988-1999, Marcel Dekker, New York.

Immediate release formulations for oral use include tablets or capsules containing the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, mannitol, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like as are found, for example, in The Handbook of Pharmaceutical Excipients, third edition, edited by Arthur H. Kibbe, American Pharmaceutical Association Washington D.C.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition may also be in the form of a buoyant tablet or capsule (i.e., a tablet or capsule that, upon oral administration, floats on top of the gastric content for a certain period of time). A buoyant tablet formulation of the compound(s) can be prepared by granulating a mixture of the antibiotic with excipients and 20-75% W/W of hydrocolloids, such as hydroxyethylcellulose, hydroxypropylcellulose, or hydroxypropyl-methylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice. Other useful controlled release compositions are known in the art (see, for example, U.S. Pat. Nos. 4,946,685 and 6,261,601).

A modified release composition may be comprised of a compression-coated core whose geometric configuration controls the release profile of the encapsulated antibiotic. By varying the geometry of the core, the profile of the antibiotic release can be adjusted to follow zero order, first order or a combination of these orders. The system can also be designed to deliver more beneficial agents at the same time, each having a different release profile (see, for example U.S. Pat. Nos. 4,111,202 and 3,279,995).

Formulations that target the Tiacumicin compounds of the present invention, specifically OPT-80 (which is composed almost entirely of the R-Tiacumicin), that release to particular regions of the intestinal tract can also be prepared. The Tiacumicin compounds of the present invention, specifically OPT-80, can be encapsulated in an enteric coating that prevents release degradation and release from occurring in the stomach, but dissolves readily in the mildly acidic or neutral pH environment of the small intestine. A formulation targeted for release of antibiotic to the colon, utilizing technologies such as time-dependent, pH-dependent, or enzymatic erosion of polymer matrix or coating can also be used.

The targeted delivery properties of the Tiacumicin compounds of the present invention, specifically OPT-80 (which is composed almost entirely of the R-Tiacumicin B), containing formulation may be modified by other means. For example, the antibiotic may be complexed by inclusion, ionic association, hydrogen bonding, hydrophobic bonding, or covalent bonding. In addition polymers or complexes susceptible to enzymatic or microbial lysis may also be used as a means to deliver drug.

Microsphere encapsulation of the Tiacumicin compounds of the present invention, specifically OPT-80 (which is composed almost entirely of the R-Tiacumicin B), is another useful pharmaceutical formulation for targeted antibiotic release. The antibiotic-containing microspheres can be used alone for antibiotic delivery, or as one component of a two-stage release formulation. Suitable staged release formulations may consist of acid stable microspheres, encapsulating the compounds of the present invention, specifically OPT-80 (which is composed almost entirely of the R-Tiacumicin B), to be released later in the lower intestinal tract admixed with an immediate release formulation to deliver antibiotic to the stomach and upper duodenum.

Microspheres can be made by any appropriate method, or from any pharmaceutically acceptable material. Particularly useful are proteinoid microspheres (see, for example, U.S. Pat. Nos. 5,601,846, or 5,792,451) and PLGA-containing microspheres (see, for example, U.S. Pat. Nos. 6,235,224 or 5,672,659). Other polymers commonly used in the formation of microspheres include, for example, poly-ε-caprolactone, poly(ε-caprolactone-Co-DL-lactic acid), poly(DL-lactic acid), poly(DL-lactic acid-Co-glycolic acid) and poly(s-caprolactone-Co-glycolic acid) (see, for example, Pitt et al., J. Pharm. Sci., 68:1534, 1979). Microspheres can be made by procedures well known in the art including spray drying, coacervation, and emulsification (see for example Davis et al. Microsphere and Drug Therapy, 1984, Elsevier; Benoit et al. Biodegradable Microspheres: Advances in Production Technologies, Chapter 3, ed. Benita, S, 1996, Dekker, New York; Microencapsulation and Related Drug Processes, Ed. Deasy, 1984, Dekker, New York; U.S. Pat. No. 6,365,187).

Powders, dispersible powders, or granules suitable for preparation of aqueous solutions or suspensions of the Tiacumicin compounds of the present invention, specifically OPT-80 (which is composed almost entirely of the R-Tiacumicin B), by addition of water are convenient dosage forms for oral administration. Formulation as a suspension provides the active ingredient in a mixture with a dispersing or wetting agent, suspending agent, and one or more preservatives. Suitable dispersing or wetting agents are, for example, naturally-occurring phosphatides (e.g., lecithin or condensation products of ethylene oxide with a fatty acid, a long chain aliphatic alcohol, or a partial ester derived from fatty acids) and a hexitol or a hexitol anhydride (e.g., polyoxyethylene stearate, polyoxyethylene sorbitol monooleate, polyoxyethylene sorbitan monooleate, and the like). Suitable suspending agents are, for example, sodium carboxymethylcellulose, methylcellulose, sodium alginate, and the like.

EXAMPLES

The following examples are provided by way of describing specific embodiments of the present invention without intending to limit the scope of the invention in any way.

Example 1

Exact Structure of R-Tiacumicin B

The exact structure of the R-Tiacumicin B (the major most active component of OPT-80) is shown below in Formula IV. The X-ray crystal structure of the R-Tiacumicin B was obtained from a colorless, parallelepiped-shaped crystal (0.08×0.14×0.22 mm) grown in methanol and is shown as an ORTEP diagram in FIG. 1. This x-ray structure confirms the structure shown below in Formula IV. The official chemical name is 3-[[[6-Deoxy-4-O-(3,5-dichloro-2-ethyl-4,6-dihydroxybenzoyl)-2-O-methyl-β-D-mannopyranosyl]oxy]-methyl]-12(R)-[[6-deoxy-5-C-methyl-4-O-(2-methyl-1-oxopropyl)-β-D-lyxo-hexopyranosyl]oxy]-11(S)-ethyl-8(S)-hydroxy-18(S)-(1(R)-hydroxyethyl)-9,13,15-trimethyloxacyclooctadeca-3,5,9,13,15-pentaene-2-one.

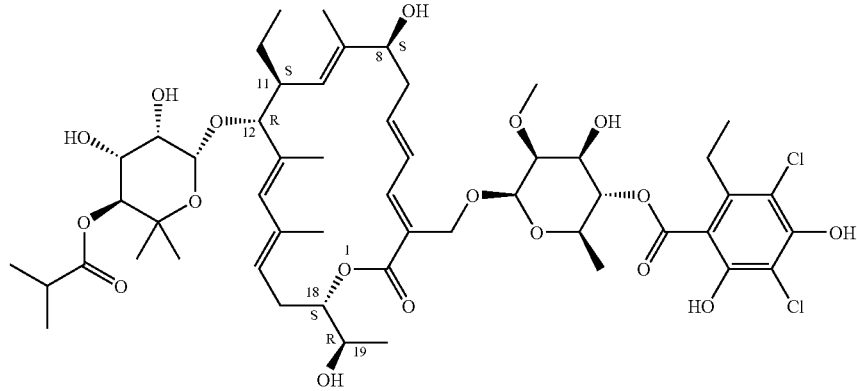

Formula IV

Example 2

Analytical Data of OPT-80 and Related Substances

The analytical data of OPT-80 (which is composed almost entirely of the R-Tiacumicin B, which is the most active component of OPT-80) and three related compounds (S-Tiacumicin B, Lipiarmycin A4, and C-19 ketone) are summarized below. The structures of these compounds are shown in Formula VIII and Table 2 below.

TABLE 2

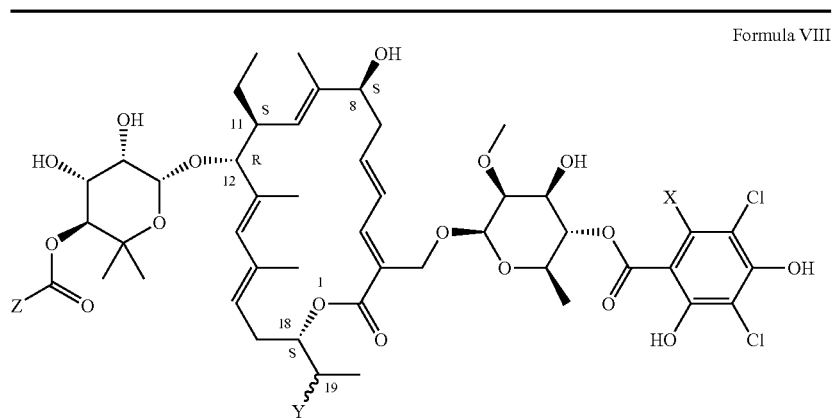

Formula VIII

Structure of R-Tiacumicin B (the major most active component of OPT-80) and related substances

| Compound | X | Y | Z |
|---|---|---|---|
| R-Tiacumicin B | Ethyl | (R)—OH | Isopropyl |
| S-Tiacumicin B | Ethyl | (S)—OH | Isopropyl |
| Lipiarmycin A4 | Methyl | (S)—OH | Isopropyl |
| C-19 Ketone | Ethyl | =O | Isopropyl |

Analytical Data of R-Tiacumicin B mp 166-169° C. (white needle from isopropanol);
$[\alpha]_D^{20}$ −6.9 (c 2.0, MeOH);
MS m/z (ESI) 1079.7 (M+Na)$^+$;
$^1$H $^1$H NMR NMR (400 MHz, CD$_3$OD) δ 7.21 (d, 1H), 6.59 (dd, 1H), 5.95 (ddd, 1H), 5.83 (br s, 1H), 5.57 (t, 1H), 5.13 (br d, 1H), 5.09 (t, 1H), 5.02 (d, 1H), 4.71 (m, 1H), 4.71 (br s, 1H), 4.64 (br s, 1H), 4.61 (d, 1H), 4.42 (d, 1H), 4.23 (m, 1H), 4.02 (pentet, 1H), 3.92 (dd, 1H), 3.73 (m, 2H), 3.70 (d, 1H), 3.56 (s, 3H), 3.52-3.56 (m, 2H), 2.92 (m, 2H), 2.64-2.76 (m, 3H), 2.59 (heptet, 1H), 2.49 (ddd, 1H), 2.42 (ddd, 1H), 2.01 (dq, 1H), 1.81 (s, 3H), 1.76 (s, 3H), 1.65 (s, 3H), 1.35 (d, 3H), 1.29 (m, 1H), 1.20 (t, 3H), 1.19 (d, 3 H), 1.17 (d, 3H), 1.16 (d, 3H), 1.14 (s, 3H), 1.12 (s, 3H), 0.87 (t, 3H);
$^{13}$C NMR (100 MHz, CD$_3$OD) δ 178.4, 169.7, 169.1, 154.6, 153.9, 146.2, 143.7, 141.9, 137.1, 137.0, 136.4, 134.6, 128.5, 126.9, 125.6, 124.6, 114.8, 112.8, 108.8, 102.3, 97.2, 94.3, 82.5, 78.6, 76.9, 75.9, 74.5, 73.5, 73.2, 72.8, 71.6, 70.5, 68.3, 63.9, 62.2, 42.5, 37.3, 35.4, 28.7, 28.3, 26.9, 26.4, 20.3, 19.6, 19.2, 18.7, 18.2, 17.6, 15.5, 14.6, 14.0, 11.4.

Analytical Data of the S-Tiacumicin B

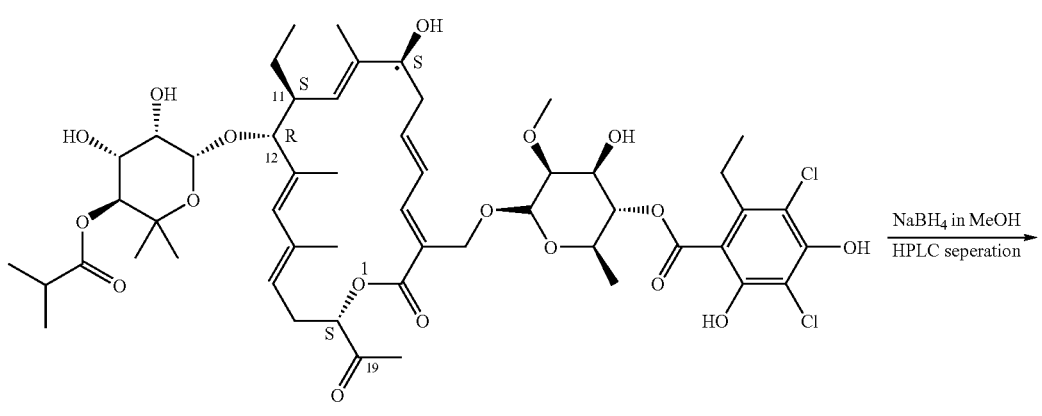

Formula II (C-19 Ketone)

-continued

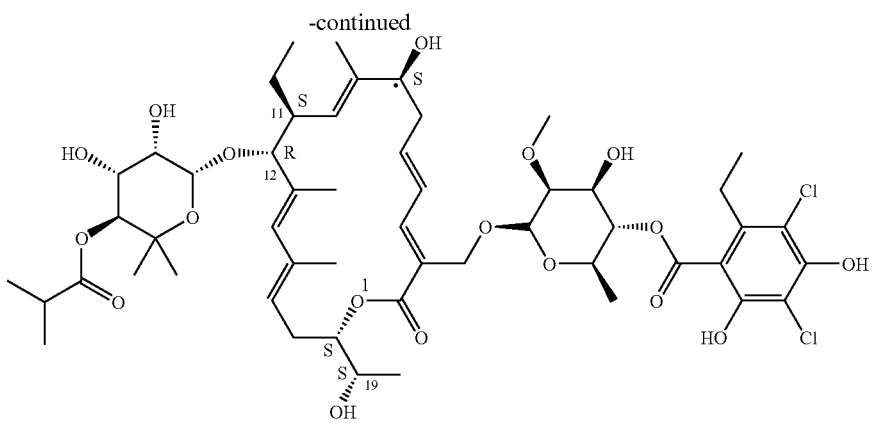

Formula V (S-Tiacumicin B)

NaBH$_4$ (9 eq, 48 mg) was added in three portions to a solution of C-19 Ketone (150 mg) in 3 mL MeOH. After 1 h, saturated NH$_4$Cl solution was added. The mixture was extracted with CHCl$_3$, and then concentrated. S-Tiacumicin B was purified by YMC-pack ODS-A 75×30 mm I.D. column (H$_2$O:MeOH:AcOH 28:72:1) yielding pure 35 mg of pure S-Tiacumicin B.

MS m/z 1074.5 (M+NH$_4$)$^+$;
$^1$H NMR (400 MHz, CDCl$_3$) δ 7.15 (d, J=11.4 Hz, 1H), 6.58 (dd, J=14.1, 11.4 Hz, 1H), 5.82 (ddd, J=14.1, 10.6, 3.5 Hz, 1H), 5.78 (s, 1H), 5.40 (dd, J=7.8, 7.8 Hz, 1H), 5.15 (dd, J=9.5, 9.5 Hz, 1H), 5.01 (d, J=9.9 Hz, 1H), 5.01 (d, J=9.9 Hz, 1H), 4.77 (ddd, J=5.8, 5.3, 5.3 Hz, 1H), 4.68 (d, J=11.6 Hz, 1H), 4.65 (br s, 1H), 4.62 (br s, 1H), 4.42 (d, J=11.6 Hz, 1H), 4.28 (br s, 1H), 4.07-3.97 (m, 2H), 3.74-3.58 (m, 4H), 3.61 (s, 3H), 3.52 (dq, J=9.5, 5.8 Hz, 1H), 3.08 (dq, J=12.6, 6.1 Hz, 1H), 3.01 (dq, J=12.6, 6.1 Hz, 1H), 2.77-2.65 (m, 2H), 2.60 (heptet, J=6.9 Hz, 1H), 2.55-2.44 (m, 3H), 1.95-1.84 (m, 1H), 1.80 (s, 3H), 1.76 (s, 3H), 1.66 (s, 3H), 1.34 (d, J=5.8 Hz, 3H), 1.29-1.24 (m, 1H), 1.27 (d, J=6.6 Hz, 3H), 1.21 (t, J=6.1 Hz, 3H), 1.19 (d, J=6.9 Hz, 3H), 1.18 (d, J=6.9 Hz, 3H), 1.15 (s, 3H), 1.10 (s, 3H), 0.84 (t, J=7.2 Hz, 3H);
$^{13}$C NMR (100 MHz, CDCl$_3$) δ 177.4, 170.1, 168.8, 157.6, 152.8, 144.4, 143.1, 141.1, 136.7, 136.2, 134.9, 133.8, 128.7, 125.7, 125.2, 123.0, 113.9, 107.5, 107.2, 101.7, 94.9, 92.6, 80.8, 79.2, 76.6, 74.8, 73.5, 72.7, 71.9, 71.7, 70.2, 70.1, 69.5, 63.5, 62.3, 41.5, 36.6, 34.3, 29.5, 28.2, 26.2, 26.0, 19.4, 19.3, 18.9, 18.5, 17.8, 17.3, 15.3, 14.1, 13.7, 11.1;

Analytical Data of Lipiarmycin A$_4$

MS m/z 1060.5 (M+NH$_4$)$^+$;
$^1$H NMR (400 MHz, CDCl$_3$) δ 7.12 (d, J=11.6 Hz, 1H), 6.59 (dd, J=14.1, 11.6 Hz, 1H), 5.85 (br s, 1H), 5.83 (ddd, J=14.1, 10.6, 4.8 Hz, 1H), 5.47 (dd, J=8.3, 8.3 Hz, 1H), 5.12 (dd, J=9.6, 9.6 Hz, 1H), 5.00 (d, J=10.1 Hz, 1H), 4.98 (br d, J=10.6 Hz, 1H), 4.75-4.69 (m, 1H), 4.68 (d, J=11.4 Hz, 1H), 4.66 (br s, 1H), 4.62 (br s, 1H), 4.40 (d, J=11.4 Hz, 1H), 4.26 (br s, 1H), 4.07-4.00 (m, 2H), 4.02 (br d, J=3.3 Hz, 1H), 3.75-3.61 (m, 4H), 3.62 (s, 3H), 3.55 (dq, J=9.6, 6.1 Hz, 1H), 2.82-2.45 (m, 6H), 2.60 (s, 3H), 2.07-1.97 (m, 1H), 1.92 (s, 3H), 1.81 (s, 3H), 1.67 (s, 3H), 1.32 (d, J=6.1 Hz, 3H), 1.30-1.22 (m, 1H), 1.21 (d, J=6.6 Hz, 3H), 1.19 (d, J=7.1 Hz, 3H), 1.18 (d, J=7.1 Hz, 3H), 1.15 (s, 3H), 1.10 (s, 3H), 0.83 (t, J=7.2 Hz, 3H);
$^{13}$C NMR (100 MHz, CDCl$_3$) δ 177.4, 170.5, 168.9, 157.8, 153.0, 144.3, 140.9, 137.7, 137.0, 136.3, 134.6, 134.4, 129.1, 127.9, 125.3, 123.2, 114.5, 107.4, 107.0, 101.8, 94.7, 92.5, 80.3, 79.6, 76.7, 74.9, 73.5, 72.7, 71.9, 71.6, 70.2, 70.1, 69.1, 63.6, 62.3, 41.9, 36.9, 34.4, 28.8, 28.2, 25.9, 20.0, 19.3, 19.0, 18.6, 18.5, 17.8, 17.2, 15.5, 13.8, 11.2;

Analytical Data of C-19 Ketone

MS m/z 1072.5 (M+NH$_4$)$^+$;
$^1$H NMR (400 MHz, CDCl$_3$) δ 7.27 (d, J=11.4 Hz, 1H), 6.61 (dd, J=14.7, 11.4 Hz, 1H), 5.91 (ddd, J=14.7, 9.1, 5.8 Hz, 1H), 5.83 (s, 1H), 5.31 (dd, J=7.9, 7.9 Hz, 1H), 5.14 (dd, J=9.7, 9.7 Hz, 1H), 5.06 (d, J=10.6 Hz, 1H), 5.00 (d, J=10.1 Hz, 1H), 4.98 (dd, J=7.1, 4.8 Hz, 1H), 4.67 (d, J=11.9 Hz, 1H), 4.66 (br s, 1H), 4.61 (br s, 1H), 4.42 (d, J=11.9 Hz, 1H), 4.30 (br s, 1H), 4.02 (br d, J=3.3 Hz, 1H), 3.63-3.60 (m, 4H), 3.62 (s, 3H), 3.51 (dq, J=9.7, 6.1 Hz, 1H), 3.09 (dq, J=14.4, 7.3 Hz, 1H), 3.03 (dq, J=14.4, 7.3 Hz, 1H), 2.76-2.50 (m, 6H), 2.21 (s, 3H), 1.93-1.87 (m, 1H), 1.87 (s, 3H), 1.75 (s, 3H), 1.63 (s, 3H), 1.32 (d, J=6.1 Hz, 3H), 1.27-1.22 (m, 1H), 1.21 (t, J=7.3 Hz, 3H), 1.19 (d, J=7.1 Hz, 3H), 1.18 (d, J=7.1 Hz, 3H), 1.14 (s, 3H), 1.10 (s, 3H), 0.84 (t, J=7.3 Hz, 3H);
$^{13}$C NMR (100 MHz, CDCl$_3$) δ 205.5, 177.4, 170.1, 166.9, 157.6, 152.8, 145.7, 143.1, 142.0, 137.1, 136.8, 135.5, 133.7, 128.3, 124.8, 124.0, 122.8, 113.9, 107.3, 107.2, 101.3, 94.8, 92.4, 80.4, 77.7, 76.6, 74.7, 73.5, 72.6, 71.8, 71.7, 70.2, 70.0, 63.0, 62.3, 41.5, 36.5, 34.3, 29.6, 28.1, 26.2, 26.1, 26.0, 19.2, 18.9, 18.5, 17.8, 17.3, 15.2, 14.0, 13.3, 11.0

Example 3

Biological Activity

MIC Values Determined for Several *C. difficile* Strains

OPT-80 (which is composed almost entirely of the R-Tiacumicin B) and its related compounds were tested against *C. difficile*. The MIC values are reported below in Table 3. OPT-80 was surprisingly active when compared to its enantiomer S-Tiacumicin B and Lipiarmycin A4.

TABLE 3

| | MIC (μg/ml) versus *C. difficile* strains | | | |
|---|---|---|---|---|
| *C. difficile* strains | R-Tiacumicin B (>90% Stereo-merically Pure) | S-Tiacu-micin B | Lipiar-mycin A4 | C-19 Ketone |
| ATCC 9689 | 0.03 | 0.125 | 0.06 | 0.06 |
| ATCC 43255 | 0.125 | 1 | 0.5 | 0.5 |

TABLE 3-continued

MIC (μg/ml) versus *C. difficile* strains

| C. difficile strains | R-Tiacumicin B (>90% Stereomerically Pure) | S-Tiacumicin B | Lipiarmycin A4 | C-19 Ketone |
|---|---|---|---|---|
| ATCC 17857 | 0.03 | 0.25 | 0.06 | nd |
| LC # 1 (Clinical isolate) | 0.125 | 1 | 0.5 | 0.5 |

MIC Values Determined for Various Microorganisms

OPT-80 (which is composed almost entirely of the R-Tiacumicin B) and its related compounds were tested against several other pathogens. The MIC values are reported below in Table 4. OPT-80 was suprisingly active when compared to S-Tiacumicin B and Lipiarmycin A4.

TABLE 4

MIC (μg/ml) against other microorganisms

| Strain ID # | Organism | R-Tiacumicin B (>90% Stereomerically Pure) | S-Tiacumicin B | Lipiarmycin A4 |
|---|---|---|---|---|
| 1 | S. aureus (ATCC 29213) | 4 | 64 | 8 |
| 2 | S. aureus, (MRSA) | 4 | 64 | 16 |
| 3 | S. aureus, (MRSA) | 4 | 64 | 8 |
| 4 | E. faecalis (ATCC 29212) | 2 | 8 | 2 |
| 5 | E. faecalis Vanc. resistant | 4 | 32 | 16 |
| 6 | E. faecalis Vanc. resistant | 1 | 16 | 4 |
| 7 | E. faecium Vanc. resistant | 1 | 8 | 4 |
| 8 | E. faecium Vanc. resistant | 1 | 32 | 32 |

Example 4

Post-Antibiotic Effect of OPT-80 in *C. difficile*

The post-antibiotic effect (PAE) of OPT-80 (which is composed almost entirely of the R-Tiacumicin B) was measured versus two strains of *C. difficile*, ATCC 43255 and a clinical isolate, LC3. Vancomycin and rifampin were tested additionally versus LC3.

The PAE at 4× the MIC was observed to be extremely long: greater than 24 hours, for both strains. Because of the long duration of this effect, an exact PAE was not calculated. Vancomycin, on the other hand, had a more normal PAE of less than an hour when used at 4× the MIC versus strain LC3.

Example 5

In Vitro Activity of OPT-80

The in vitro efficacy of OPT-80 (which is composed almost entirely of the R-Tiacumicin B), metronidazole, and vancomycin were assessed versus 110 genetically distinct clinical isolates of *C. difficile* via agar dilution. The MIC data are presented in Tables 5 and 6.

TABLE 5

Geometric mean, MIC ranges, $MIC_{50}$, and $MIC_{90}$ values for OPT-80 against 110 *C. difficile* clinical isolates, vancomycin, and metronidazole, in μg/mL.

| | Range | Geometric Mean | $MIC_{50}$ | $MIC_{90}$ |
|---|---|---|---|---|
| OPT-80 | 0.015-0.25 | 0.08 | 0.125 | 0.125 |
| Metronidazole | 0.025-0.5 | 0.15 | 0.125 | 0.25 |
| Vancomycin | 0.06-4 | 0.8 | 1 | 1 |

TABLE 6

Raw MIC data for OPT-80, vancomycin (VAN), and metronidazole (MTZ) versus 110 clinical isolates of *C. difficile*, in μg/mL.

| ORG ID | R-Tiacumicin B (>90% Stereomerically Pure) | MTZ | VAN |
|---|---|---|---|
| A1 1535 | 0.125 | 0.25 | 1 |
| B1 832 | 0.06 | 0.125 | 1 |
| D1 1360 | 0.03 | 0.25 | 1 |
| E1 816 | 0.06 | 0.125 | 1 |
| F1 1015 | 0.125 | 0.125 | 1 |
| G1 1077 | 0.125 | 0.125 | 1 |
| I1 1389 | 0.125 | 0.125 | 1 |
| J1 5971 | 0.06 | 0.25 | 1 |
| J7 4224 | 0.03 | 0.125 | 1 |
| J9 4478 | 0.06 | 0.125 | 1 |
| K1 4305 | 0.125 | 0.25 | 0.5 |
| K14 5780 | 0.125 | 0.125 | 1 |
| L1 1423 | 0.125 | 0.125 | 0.5 |
| N1 471 | 0.125 | 0.125 | 0.5 |
| O1 1861 | 0.06 | 0.125 | 1 |
| R1 397 | 0.125 | 0.125 | 1 |
| R6 6015 | 0.015 | 0.25 | 2 |
| V1 1521 | 0.125 | 0.125 | 0.5 |
| W1 3931 | 0.125 | 0.5 | 1 |
| X1 1890 | 0.125 | 0.125 | 1 |
| Y1 5639 | 0.06 | 0.125 | 0.5 |
| Y2 1459 | 0.06 | 0.125 | 1 |
| Z1 3036 | 0.03 | 0.125 | 1 |
| AA2 4380 | 0.015 | 0.125 | 1 |
| AB2 1725 | 0.06 | 0.125 | 1 |
| AC1 1546 | 0.06 | 0.125 | 1 |
| AF1 1808 | 0.125 | 0.125 | 0.5 |
| AG1 3044 | 0.125 | 0.125 | 1 |
| AH1 3430 | 0.125 | 0.25 | 0.5 |
| AJ1 1557 | 0.06 | 0.125 | 1 |
| AL1 1753 | 0.06 | 0.125 | 0.5 |
| AN1 464 | 0.125 | 0.125 | 0.5 |
| AO1 287 | 0.125 | 0.125 | 1 |
| AS1 4099 | 0.125 | 0.125 | 1 |
| AT1 1216 | 0.125 | 0.125 | 1 |
| AV1 941 | 0.25 | 0.125 | 0.5 |
| CJ1 893 | 0.125 | 0.025 | 1 |
| AW1 4501 | 0.125 | 0.125 | 1 |
| BE1 4307 | 0.125 | 0.25 | 1 |
| BH1 4506 | 0.06 | 0.06 | 0.5 |
| BI1 1675 | 0.125 | 0.125 | 1 |
| BK1 4291 | 0.125 | 0.125 | 0.5 |
| BL1 716 | 0.125 | 0.125 | 1 |
| BM1 1453 | 0.06 | 0.125 | 1 |
| BN1 1322 | 0.125 | 0.25 | 1 |
| BR1 1321 | 0.06 | 0.125 | 1 |
| BT1 706 | 0.06 | 0.125 | 1 |
| BV1 1183 | 0.125 | 0.25 | 1 |
| BW1 3130 | 0.125 | 0.125 | 1 |
| BX1 4271 | 0.125 | 0.25 | 1 |
| CN1 667 | 0.25 | 0.25 | 1 |
| CB1 1584 | 0.25 | 0.125 | 1 |
| CF1 5922 | 0.125 | 0.125 | 1 |
| CG1 1566 | 0.125 | 0.125 | 1 |
| CL1 3851 | 0.25 | 0.125 | 1 |
| CO1 4652 | 0.25 | 0.125 | 1 |
| CP1 5491 | 0.125 | 0.25 | 1 |
| 61 5930 | 0.03 | 0.25 | 1 |

TABLE 6-continued

Raw MIC data for OPT-80, vancomycin (VAN), and metronidazole (MTZ) versus 110 clinical isolates of *C. difficile*, in μg/mL.

| ORG ID | R-Tiacumicin B (>90% Stereomerically Pure) | MTZ | VAN |
|---|---|---|---|
| 63 6029 | 0.25 | 0.25 | 0.06 |
| 64 5940 | 0.125 | 0.25 | 1 |
| 65 5967 | 0.06 | 0.25 | 0.5 |
| 66 6366 | 0.015 | 0.125 | 0.5 |
| 67 6367 | 0.125 | 0.25 | 1 |
| 68 6368 | 0.03 | 0.125 | 0.06 |
| 69 6370 | 0.25 | 0.25 | 0.5 |
| 70 6376 | 0.125 | 0.25 | 2 |
| 71 6379 | 0.125 | 0.25 | 1 |
| 72 6380 | 0.125 | 0.25 | 2 |
| 73 6382 | 0.25 | 0.25 | 1 |
| 75 6388 | 0.125 | 0.125 | 0.5 |
| 76 6389 | 0.125 | 0.25 | 0.5 |
| 77 6390 | 0.06 | 0.125 | 1 |
| 78 6392 | 0.015 | 0.03 | 0.5 |
| 80 6327 | 0.125 | 0.125 | 0.5 |
| 81 6328 | 0.125 | 0.125 | 0.5 |
| 82 6329 | 0.06 | 0.03 | 0.5 |
| 83 6330 | 0.06 | 0.125 | 0.5 |
| 84 6331 | 0.125 | 0.25 | 0.5 |
| 85 6332 | 0.06 | 0.125 | 1 |
| 86 6333 | 0.03 | 0.125 | 0.5 |
| 87 6334 | 0.125 | 0.125 | 0.5 |
| 88 6335 | 0.125 | 0.25 | 0.5 |
| 89 6336 | 0.25 | 0.5 | 1 |
| 90 6338 | 0.125 | 0.125 | 1 |
| 91 6339 | 0.125 | 0.125 | 1 |
| 93 6341 | 0.125 | 0.125 | 1 |
| 94 6343 | 0.015 | 0.06 | 0.5 |
| 95 6347 | 0.125 | 0.125 | 1 |
| 96 6348 | 0.06 | 0.125 | 0.5 |
| 97 6349 | 0.25 | 0.125 | 1 |
| 98 6350 | 0.125 | 0.5 | 1 |
| 101 6354 | 0.015 | 0.06 | 1 |
| 102 6355 | 0.016 | 0.125 | 1 |
| 103 6068 | 0.06 | 0.125 | 1 |
| 104 6060 | 0.03 | 0.25 | 1 |
| 105 6071 | 0.03 | 0.125 | 0.5 |
| 106 6078 | 0.03 | 0.25 | 0.5 |
| 107 6079 | 0.06 | 0.125 | 0.5 |
| 109 6274 | 0.015 | 0.125 | 1 |
| 111 6279 | 0.03 | 0.125 | 1 |
| 112 6280 | 0.06 | 0.125 | 0.5 |
| 113 6304 | 0.06 | 0.125 | 1 |
| 114 386 | 0.06 | 0.125 | 4 |
| 115 5985 | 0.015 | 0.25 | 2 |
| 116 5702 | 0.06 | 0.125 | 1 |
| 117 6026 | 0.06 | 0.125 | 2 |
| 120 6057 | 0.03 | 0.25 | 1 |
| 121 6072 | 0.06 | 0.25 | 0.5 |
| 122 6111 | 0.25 | 0.25 | 0.5 |
| 100 6353 | 0.125 | 0.25 | 1 |

Example 6

Activity of OPT-80 Compared Against Selected Anaerobic Species

The in vitro activity of OPT-80 was determined against 350 anaerobes. The experimental procedure for which is outlined in Antimicrobial Agents and Chemotherapy, 2004, 48: 4430-4434, which is hereby incorporated by reference in its entirety.

All organisms, including the 21 *C. difficile* strains, were separate isolates and not clonally related. All quality-control gram-negative and -positive strains recommended by NCCLS were included with each run: in every case, results (where available) were in range.

Results of MIC testing are presented in Table 7.

TABLE 7

MICs (μg/ml) of R-Tiacumicin B (>90% Stereomerically Pure)

| Organism | MIC range | $MIC_{50}$ | $MIC_{90}$ |
|---|---|---|---|
| *Bacteroides fragilis* (19) | 64->128 | >128 | >128 |
| Non-*fragilis B. fragilis* group species (38) | 64->128 | >128 | >128 |
| *Prevotella/Porphyromonas* species (42) | 16->128 | >128 | >128 |
| *Fusobacterium nucleatum* (14) | 64->128 | >128 | >128 |
| *Fusobacterium mortiferum* (10) | 64->128 | >128 | >128 |
| *Fusobacterium* species, miscellaneous (14) | 16->128 | >128 | >128 |
| *Peptostreptococcus tetradius* (16) | 0.25-2.0 | 1.0 | 1.0 |
| *Peptostreptococcus asaccharolyticus* (15) | 0.25-1.0 | 0.5 | 1.0 |
| *Peptostreptococcus anaerobius* (15) | <0.016-0.03 | <0.016 | <0.016 |
| *Finegoldia magna* (15) | 0.25-2.0 | 1.0 | 1.0 |
| *Micromonas micros* (14) | <0.016-0.06 | 0.03 | 0.06 |
| *Peptostreptococcus prevotii* (3) | 0.25-1.0 | NA | NA |
| *Propionibacterium acnes* (20) | 0.5-1.0 | 4.0 | 4.0 |
| *Eggerthella lenta* (10) | <0.016-0.06 | <0.016 | <0.03 |
| Miscellaneous gram-positive non-spore-forming rods (20) | <0.016-16 | <0.125 | 16 |
| *Clostridium perfringens* (35) | <0.016-0.06 | <0.016 | 0.03 |
| *Clostridium difficile* (21) | <0.016-0.25 | <0.016 | 0.125 |
| *Clostridium tertium* (10) | <0.016-0.06 | <0.016 | 0.03 |
| *Clostridium* species (19) | <0.016-0.06 | <0.016 | 0.03 |
| *Clostridium* spp. (all) (85) | <0.016-0.06 | <0.016 | 0.06 |

Example 7

In Vitro Activities of OPT-80 Against Intestinal Bacteria

The in vitro activity of OPT-80 against intestinal bacteria was evaluated. The experimental procedure for which is outlined in Antimicrobial Agents and Chemotherapy, 2004, 48: 4898-4902, which is hereby incorporated by reference in its entirety.

Antimicrobial concentration ranges were selected to encompass or surpass the levels that would be achieved in the gut (to the extent that this information is available), subject to the limitations of solubility of the drugs in the testing medium. The range of concentration of OPT-80 used during testing was 0.03 μg/ml to 1024 μg/ml.

For analysis, the bacteria tested were generally placed into genus, species, or other groups with at least 10 isolates. The ranges and the MICs at which 50 and 90% of isolates were inhibited were determined except for organisms with fewer than 10 strains tested, for which only the ranges are reported (Table 8).

OPT-80 had good activity against most anaerobic gram-positive non-spore-forming rods and anaerobic gram-positive cocci. OPT-80 also showed good activity against enterococci and staphylococci.

TABLE 8

In vitro activity of R-Tiacumicin B (>90% Stereomerically Pure) against 453 bacterial isolates

| Organism | MIC range | MIC$_{50}$ | MIC$_{90}$ |
| --- | --- | --- | --- |
| *Bacteroides fragilis* group spp. (50) | 256–>1024 | 256 | >1024 |
| *Veillonella* spp. (10) | 16-128 | 32 | 128 |
| Other anaerobic gram-negative rods (51) | 0.06-1024 | 1024 | >1024 |
| All anaerobic gram-negative species (111) | 0.06–>1024 | 256 | >1024 |
| *Clostridium bifermentans* (9) | 0.06 | NA | NA |
| *Clostridium bolteae* (7) | 1-64 | NA | NA |
| *Clostridium clostridioforme* (4) | 4-128 | NA | NA |
| *Clostridium difficile* (23) | 0.06-2 | 0.12 | 0.25 |
| *Clostridium glycolicum* (9) | 0.06-1 | NA | NA |
| *Clostridium innocuum* (9) | 32-128 | NA | NA |
| *Clostridium paraputrificum* (8) | 0.06-8 | NA | NA |
| *Clostridium perfringens* (14) | 0.06 | 0.062 | 0.062 |
| *Clostridium ramosum* (10) | 256-512 | 512 | 512 |
| *Clostridium sordellii* (5) | 0.06 | NA | NA |
| Other clostridial species (9) | 0.06–>1024 | NA | NA |
| All *Clostridium* species (107) | 0.06–>1024 | 0.062 | 128 |
| Anaerobic non-spore-forming gram-positive rods (63) | 0.06–>1024 | 1 | 32 |
| Anaerobic gram-positive cocci (49) | 0.06–>1024 | 0.5 | 2 |
| All anaerobic gram-positive species (219) | 0.06–>1024 | 0.12 | 64 |
| *Streptococcus*, formerly *S. milleri* group (14) | 16-64 | 32 | 32 |
| Other *Streptococcus* species (9) | 16-128 | NA | NA |
| *Enterococcus* species (21) | 2.0-16 | 8 | 8 |
| *Staphylococcus aureus* and *Staphylococcus epidermidis* (19) | 0.25-2 | 0.5 | 2 |
| Total for all strains (453) | 0.06–>1024 | 8 | 1024 |

Other Embodiments

All references discussed above are herein incorporated by reference in their entirety for all purposes. While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method of treating diarrhea caused by *C. difficile* gastrointestinal infection in a human patient in need thereof comprising orally administering to said patient a therapeutically effective amount of a compound having the formula (IV):

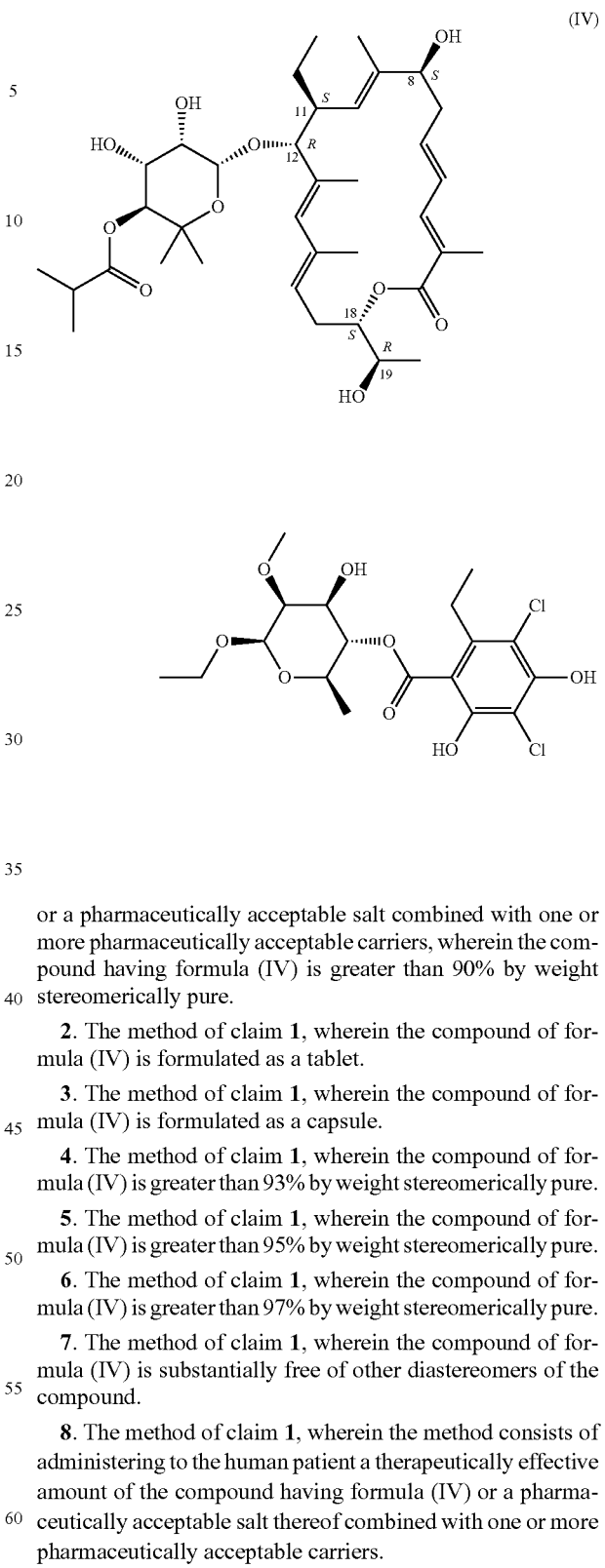

or a pharmaceutically acceptable salt combined with one or more pharmaceutically acceptable carriers, wherein the compound having formula (IV) is greater than 90% by weight stereomerically pure.

2. The method of claim 1, wherein the compound of formula (IV) is formulated as a tablet.

3. The method of claim 1, wherein the compound of formula (IV) is formulated as a capsule.

4. The method of claim 1, wherein the compound of formula (IV) is greater than 93% by weight stereomerically pure.

5. The method of claim 1, wherein the compound of formula (IV) is greater than 95% by weight stereomerically pure.

6. The method of claim 1, wherein the compound of formula (IV) is greater than 97% by weight stereomerically pure.

7. The method of claim 1, wherein the compound of formula (IV) is substantially free of other diastereomers of the compound.

8. The method of claim 1, wherein the method consists of administering to the human patient a therapeutically effective amount of the compound having formula (IV) or a pharmaceutically acceptable salt thereof combined with one or more pharmaceutically acceptable carriers.

9. A method of treating diarrhea caused by *C. difficile* gastrointestinal infection in a human patient in need thereof consisting of orally administering to said patient a therapeutically effective amount of a compound having the formula (IV):

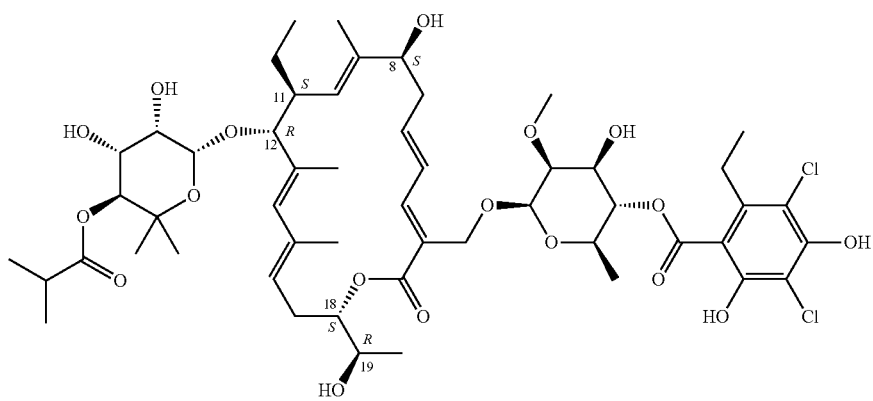

(IV)

or a pharmaceutically acceptable salt thereof combined with one or more pharmaceutically acceptable carriers, wherein the compound of the formula (IV) is greater than 93% by weight stereomerically pure.

10. The method of claim 9, wherein the compound of formula (IV) is formulated as a tablet.

11. The method of claim 9, wherein the compound is formulated as a capsule.

12. The method of claim 9, wherein the compound of formula (IV) is greater than 95% by weight stereomerically pure.

13. The method of claim 9, wherein the compound of formula (IV) is greater than 97% by weight stereomerically pure.

14. The method of claim 9, wherein the compound of formula (IV) is substantially free of other diastereomers of the compound.

* * * * *

UNITED STATES PATENT AND TRADEMARK OFFICE
CERTIFICATE OF CORRECTION

| | | |
|---|---|---|
| PATENT NO. | : 7,906,489 B2 | Page 1 of 1 |
| APPLICATION NO. | : 11/882219 | |
| DATED | : March 15, 2011 | |
| INVENTOR(S) | : Youe-Kong Shue et al. | |

It is certified that error appears in the above-identified patent and that said Letters Patent is hereby corrected as shown below:

In claim 1 (column 30, lines 1-36), Formula IV should appear as follows:

(IV)

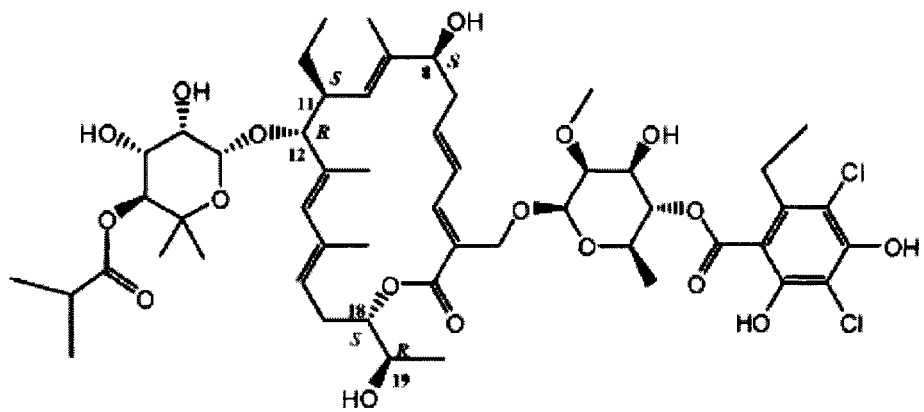

Signed and Sealed this
Seventh Day of June, 2011

David J. Kappos
*Director of the United States Patent and Trademark Office*